United States Patent [19]

Sengewald

[11] Patent Number: 4,770,911

[45] Date of Patent: Sep. 13, 1988

[54] OPERATION TABLE COVER AND METHOD OF MAKING THE SAME

[76] Inventor: Karl H. Sengewald, Kreisstr. 16, 4802 Halle in Westfalen, Fed. Rep. of Germany

[21] Appl. No.: 865,543

[22] Filed: May 20, 1986

[30] Foreign Application Priority Data

Jun. 1, 1985 [DE] Fed. Rep. of Germany ....... 3519705

[51] Int. Cl.$^4$ .............................................. B65D 65/02
[52] U.S. Cl. ..................................... 428/35; 428/124; 428/130; 428/224
[58] Field of Search ................. 428/35, 124, 130, 224

[56] References Cited

U.S. PATENT DOCUMENTS 4,560,598 12/1985 Cowan ................................... 428/35

Primary Examiner—John E. Kittle
Assistant Examiner—James J. Seidleck
Attorney, Agent, or Firm—Michael J. Striker

[57] ABSTRACT

An operation table cover formed of a hose closed at one end and open at the other end. The open end has two bent-over portions. The closed end of the cover is insertable into the pocket formed by the bent-over portion on the upper face of the cover. The cover has in the region of the bent-over portion an expanded part. A device for making the expanding part by elastically deforming the hose portion by means of two counter rollers is also provided.

1 Claim, 3 Drawing Sheets

FIG.8
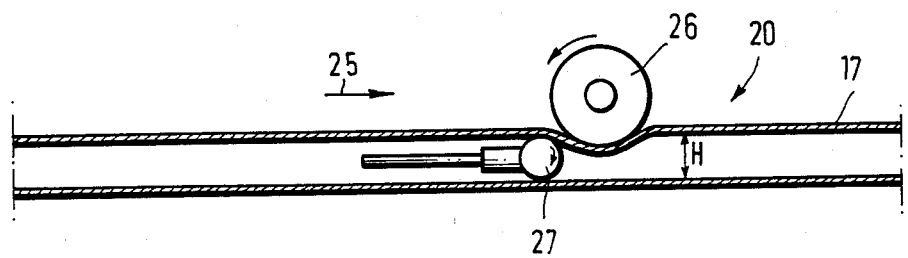
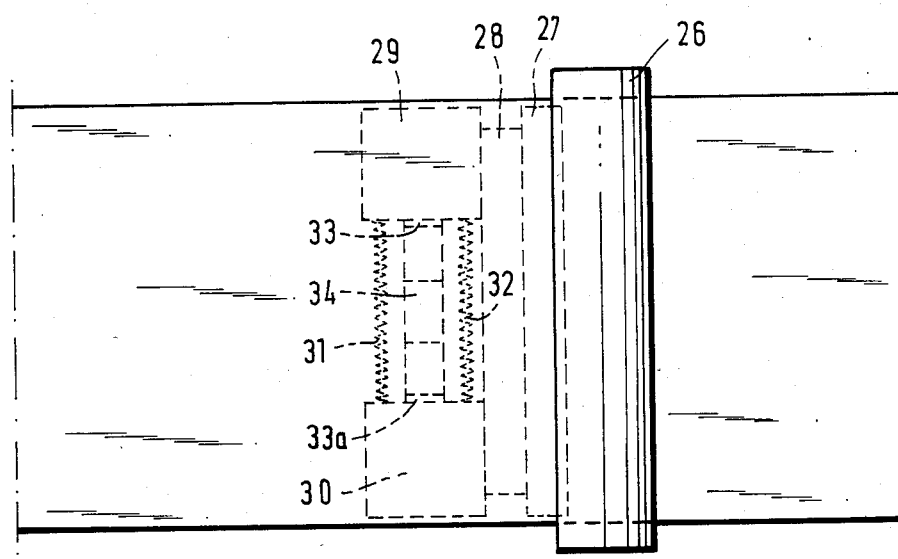
FIG.9

OPERATION TABLE COVER AND METHOD OF MAKING THE SAME

BACKGROUND OF THE INVENTION

The present invention relates to an operation table cover or hood in general, and more specifically to a hood for covering the operation table, made of a hose of thermoplastic foil.

The cover of the type under discussion is made of the hose which has an open end and is usually pulled over the upper plate of the operation table to cover the latter. The upper surface of such a cover is normally provided with a coating made of absorptive non-woven fabric.

The cover has in the region of its open end a fold, the purpose of which resides in that the cloth or non-woven fabric contacts the fold, and the fold is pulled over the supporting flange of the table. With the comparatively long, often 1.20 or up to 2 m long, table cover, the cover, upon being pulled over the operation table should not touch the ground and therefore it is folded whereby the end of the hose, opposite to the fold is to be inserted into the fold so that, during the slipping over, the free end can pulled out from the fold and its contact with the ground in the operation room would be prevented.

In conventional operation table covers, the folds at the open end of the hose have been made by hand which is quite bothersome. Also, the folds made by hand have often various widths. Since upon the formation of the fold by hand the thermoplastic foil can be stretched within the range of its stability the fold is very stiff. Therefore the insertion of the hose end, opposite to that of the fold, into the fold becomes difficult.

SUMMARY OF THE INVENTION

It is an object of the present invention to provide an improved operation table cover.

It is another object of the invention to provide a cover for an operation table, in which the fold can be formed in a very simple manner by simple mechanical means.

These and other objects of the invention are attained by an operation table cover formed of a hose of thermoplastic foil and having a closed end and an opposite open end, said hose having at said open end at least one fold so that the hose can be pulled over a supporting flange of an operation table, said hose having an upper surface provided with a coating of an absorptive non-woven fabric, the width of the hose in the region of said fold being permanently enlarged relative to a remaining part of the hose.

In the cover of the invention, the inner width in the region of the fold is expanded or enlarged, and such an expansion is obtained that, when a small expansion remains, the fold produced after the expansion is simplified.

The closed end of the hose opposite to the fold can be easily inserted into the pocket or recess formed by the fold. Since this insertion is simplified by the expansion the insertion can be easily carried out mechanically.

The objects of the invention are further attained by a method of forming an operation table cover of a hose of thermoplastic foil and having a closed end and an opposite open end provided with at least one fold and being widened in the region of the fold, the method comprising the steps of forming a hose of thermoplastic foil with one end closed; forming an expanded portion on the hose over a width corresponding to the width of the fold mechanically be deforming a portion of the hose by an amount exceeding an elastic deformation; and bending said expanded portion over a non-expanded portion of the hose.

A step of forming a tongue at said open end of the hose can be carried out in the method of the invention.

The tongue may be formed of two portions which are displaceable transversely of an axis of elongation of the hose.

The method may further include the step of placing said tongue inside the hose and providing a drive within the hose for expanding the hose in a limited region by moving said tongue in the direction transverse to said axis of elongation by means of said drive. Thereby it is obtained that bending or turning over the portion of the hose is manufactured in such a manner that the transverse seam welding and a corresponding cutting off the hose and a limiting expanding of the portion of the hose to form the fold are carried out in one single functional unit. The cover is not firstly shaped into an elongated bag or package whereby individual bags are expanded at their open ends and only then are bent over to form the folds. This results in producing covers of hoses provided with folds formed in manufacturing machines rather than by hand.

The advantage of the method of the invention resides in that a sterile production of operation table covers provided with folds can be obtained, and stacking of such covers in a container, after the covers have been produced, is possible.

With conventional methods, folds or flanges have been made by hand, which has brought danger of contaminating the operation table cover with germs. The operation in a germ-free environment has been difficult and involved additional expenses to prevent this.

These expenses are avoided because due to the invention, the cover and the flange or fold are made in a single manufacturing unit, and with comparatively low costs a satisfactory sterilization can be obtained because only the space of the processing machine and a closed packing device should be kept sterile, which space is maintained relatively small.

The aforementioned drive may include electromagnets which can be operated from outside of the hose.

The method may further include the step of providing a rotatable roller on an upper wall of the hose, said drive and said tongue being supported against said roller and providing a support roller inside the hose, said rotatable roller cooperating with said support roller from outside the hose to increase an inner height of the hose in the region of said rollers.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

FIG. 8 is schematic view of the expanding device positioned inside the hose; and FIG. 9 is the top plan view of the device of FIG. 8.

DETAILED DESCRIPTION OF THE PREFERRED EMBODIMENTS

Figure 1:
FIG. 1 is a perspective view of the cover of the operation table, according to the invention.

Referring now to the drawings it will be seen that an operation table cover or hood 10 is comprised of a hose of thermoplastic synthetic material. The operation table cover made of the hose has at one end thereof a transverse weld seam 11 in connection with a perforation or separation cut 12. A turn-over portion 13 is provided at the other end of the hose.

Figure 2:
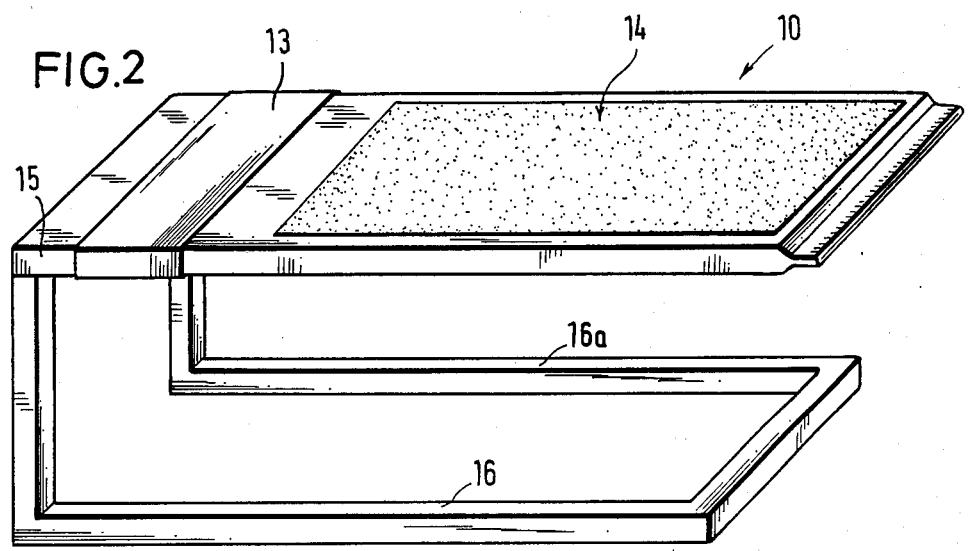
FIG. 2 is a perspective view of the operation table with the cover of FIG. 1, slipped over the table.

FIG. 2 shows the cover, on the upper surface of which a coating 14 of non-woven fabric is provided. The cover overlaps an operation table 15 which has feet 16 and 16a.

Figure 3:
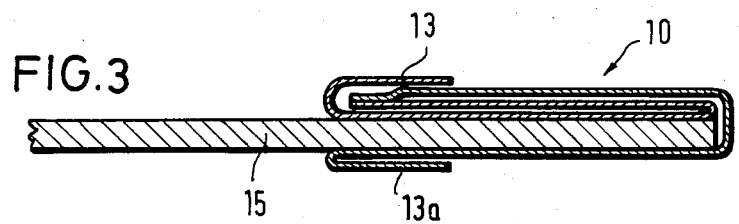
FIG. 3 is a sectional view of the portion of the table plate with the cover partially covering the plate.
Figure 4:
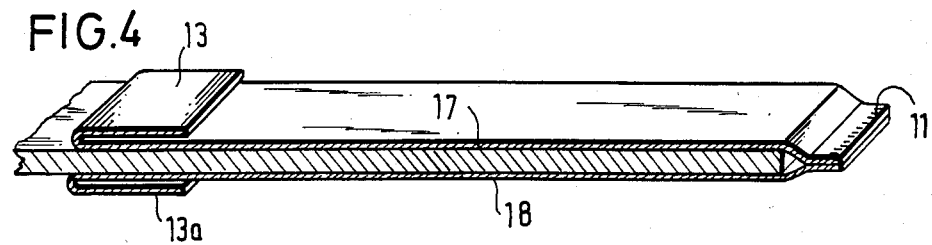
FIG. 4 is a vertical sectional view through the table plate with the cover completely overlaying the same.

FIGS. 3 and 4 illustrate the table 15 with a partially overlapping cover 10. The upper fold or portion 13 and the lower fold or portion 13a are formed, wherein the upper fold 13 is the extension of the upper foil layer 17 and the lower fold 13a is the extension of the lower foil layer 18. The closed end with the transversal weld seam 11 can be inserted into the upper fold 13 to prevent this end from appearing at the feet.

Figure 5:
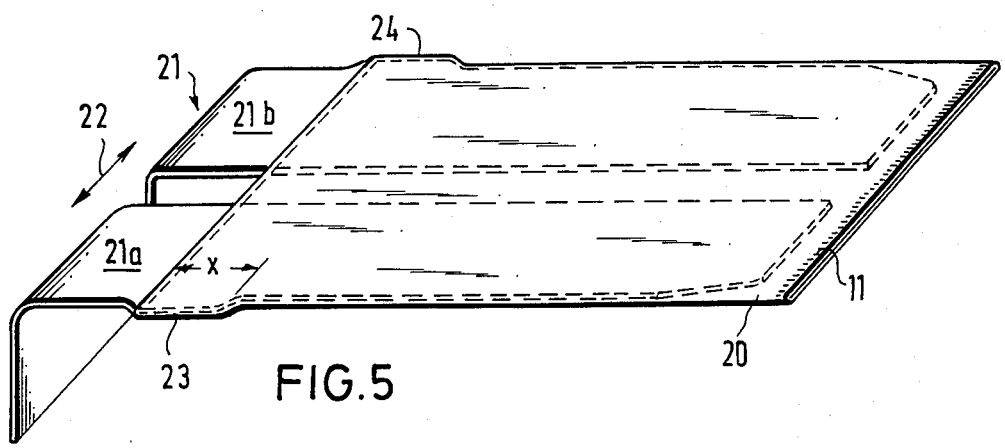
FIG. 5 is the operation table cover with the tongue and widening portions.
Figure 6:
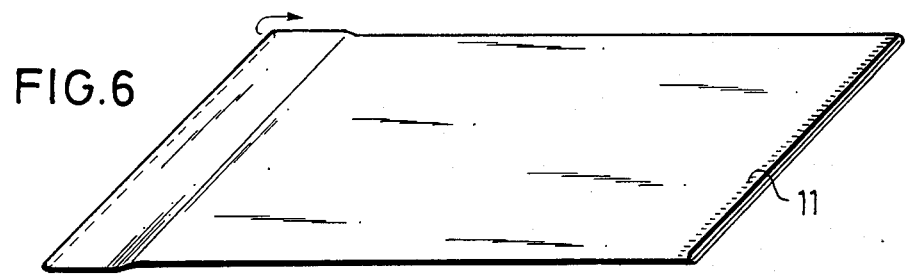
FIG. 6 is a top plan view of the cover with a widening portion.
Figure 7:
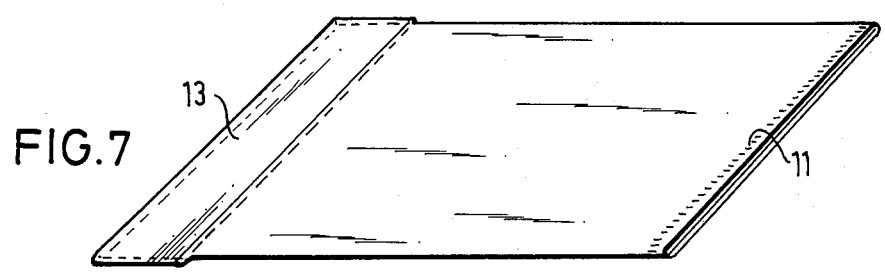
FIG. 7 is a view of the cover with the fold.

FIG. 5 shows a step of the method of producing the cover from the hose, wherein a tongue 21 is provided on the hose 20 formed by walls 17 and 18, this tongue including two portions 21a and 21b which are movable in the directions of arrow 22 away from each other and thereby transversely to the direction of elongation of hose 20. Furthermore two edges of the hose have expanded portions 23, 24 extended over the distance X. As shown in FIG. 6 these expanded portions are advantageous because the expansion can be obtained due to the elasticity range of the foil or film of the which the hose is formed. The formation of folds 13 and 13a becomes possible due to the provision of the expanded portions 23, 24.

Referring to FIGS. 8, 9, a device for forming expanded portions in the hose 20 is shown. This device includes a rotating roller 26 placed on the upper wall 17 of the hose 20 movable in the direction of arrow 25. Roller 26 extends transversely of the elongation of the hose and rotates to produce the decrease in the inner height H of the hose while an inner roller 27, placed between the walls 17 and 18 and rotating in the direction counter to that of roller 26, forms expanded portions. The inner roller 27 is provided with a rail 28 on which two tongues 29 and 30 are slidably movable transversely to the elongation of the hose. Tongues 29 and 30 are pulled inwardly by tension springs 31 and 32. Respective stops 33 and 33a limit the movement of the tongues. The movement of two tongues 29 and 30 outwardly for expanding the hose is obtained by electromagnets 34.

The expanding device arranged in the hose makes possible the manufacture of the operation table covers with folds in one mechanical unit.

It will be understood that each of the elements described above, or two or more together, may also find a useful application in other types of operation table covers and methods of making the same differing from the types described above.

While the invention has been illustrated and described as embodied in an operation table cover and a method of making the same, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. In an operation table cover formed of a hose of thermoplastic foil having a closed end and an opposite open end, said hose having at said open end at least one fold formed by folding said open end on itself so that the hose can be pulled over a supporting flange of an operation table, said hose having an upper surface provided with a coating of an absorptive non-woven fabric, the improvement comprising that the width of said hose in the region of said fold is enlarged relative to a remaining part of the hose so that producing of said fold and insertion of said open end of said hose into a pocket formed by said fold is more easily achieved.

* * * * *